US006855732B2

(12) United States Patent
Neogi et al.

(10) Patent No.: US 6,855,732 B2
(45) Date of Patent: Feb. 15, 2005

(54) COMPOUNDS TO TREAT DIABETES AND ASSOCIATED CONDITIONS

(75) Inventors: Partha Neogi, Fremont, CA (US); Bishwajit Nag, Fremont, CA (US); Frederick J. Lakner, Hayward, CA (US); Debendranath Dev, Fremont, CA (US); Satyanarayana Medicherla, Sunnyvale, CA (US)

(73) Assignee: Theracos, Inc., Sunnyvale, CA (US)

( * ) Notice: Subject to any disclaimer, the term of this patent is extended or adjusted under 35 U.S.C. 154(b) by 0 days.

(21) Appl. No.: 10/075,442

(22) Filed: Feb. 15, 2002

(65) Prior Publication Data

US 2002/0107285 A1 Aug. 8, 2002

Related U.S. Application Data

(62) Division of application No. 09/436,047, filed on Nov. 8, 1999, now Pat. No. 6,525,093.

(51) Int. Cl.[7] ............................................. A01N 37/34
(52) U.S. Cl. ........................ 514/521; 560/55; 568/592
(58) Field of Search .......................... 514/521; 560/55; 568/592

(56) References Cited

U.S. PATENT DOCUMENTS

| 3,609,183 A | | 9/1971 | DeWald et al. |
|---|---|---|---|
| 3,683,009 A | | 8/1972 | Middleton |
| 3,857,955 A | * | 12/1974 | Marshall ..................... 424/340 |
| 4,110,470 A | * | 8/1978 | Kummer et al. ............ 424/309 |
| 4,217,366 A | | 8/1980 | Kikumoto et al. |
| 4,271,186 A | | 6/1981 | Forster et al. |
| 4,284,637 A | | 8/1981 | Kikumoto et al. |
| 4,310,534 A | | 1/1982 | Kikumoto et al. |
| 4,312,855 A | | 1/1982 | Grand |
| 4,326,055 A | | 4/1982 | Loeliger |
| 4,389,416 A | * | 6/1983 | Plattner ..................... 424/309 |
| 4,716,905 A | | 1/1988 | Schmued |
| 4,866,086 A | | 9/1989 | Boyle et al. |
| 4,929,635 A | | 5/1990 | Coquelet et al. |
| 4,940,707 A | | 7/1990 | Klaus et al. |
| 4,992,576 A | * | 2/1991 | Gapinski .................... 514/454 |
| 5,087,637 A | | 2/1992 | Janssen et al. |
| 5,162,337 A | | 11/1992 | Elbrecht et al. |
| 5,171,753 A | | 12/1992 | Munson, Jr. et al. |
| 5,189,056 A | | 2/1993 | Orlando et al. |
| 5,246,936 A | | 9/1993 | Treacy et al. |
| 5,250,562 A | | 10/1993 | Klaus et al. |
| 5,314,693 A | | 5/1994 | Suga |
| 5,378,705 A | | 1/1995 | Klaus et al. |
| 5,409,953 A | | 4/1995 | Pettit et al. |
| 5,430,062 A | | 7/1995 | Cushman et al. |
| 5,494,932 A | | 2/1996 | Cardin et al. |
| 5,521,160 A | | 5/1996 | Chucholowski et al. |
| 5,525,632 A | | 6/1996 | Obsumi et al. |
| 5,532,129 A | | 7/1996 | Heller |
| 5,559,151 A | | 9/1996 | Adorante et al. |
| 5,565,191 A | | 10/1996 | Raspanti |
| 5,565,322 A | | 10/1996 | Heller |
| 5,569,786 A | | 10/1996 | Pettit et al. |
| 5,583,128 A | | 12/1996 | Bhatnagar |
| 5,589,506 A | | 12/1996 | Hashimoto et al. |
| 5,672,625 A | | 9/1997 | Cardin et al. |
| 5,674,906 A | | 10/1997 | Hatanaka et al. |
| 5,705,530 A | | 1/1998 | Adorante et al. |
| 5,716,928 A | | 2/1998 | Benet et al. |
| 5,731,353 A | | 3/1998 | Ohsumi et al. |
| 5,733,909 A | | 3/1998 | Black et al. |
| 5,767,268 A | | 6/1998 | Chucholowski et al. |
| 5,770,620 A | | 6/1998 | Mjalli et al. |
| 5,827,898 A | | 10/1998 | Khandwala et al. |

FOREIGN PATENT DOCUMENTS

JP            63290842      * 11/1988

OTHER PUBLICATIONS

Baker et al, CA (chemical Abstract) 126:59751 abstract for WO 9634651 (1997).*
Shono et al CA 112:206735 abstract for JP 01222078 (1990).*
Tian et al, CA 121:42116 abstract for Zhongguo Huanjing Kexue (1994).*
Baker et al, CA 126:59751 abstract for WO 9634651 (1997).*
Shono et al CA 112:206735 abstract for JP 01222078 (1990).*
Tian et al, CA 121:42116 abstract for Zhongguo Huanjing Kexue (1994).*
Dygos et al, Journal of Medicinla Chemistry, 1977, vol. 20, No. 12, pp. 1705–1708.*
Pettit et al. "Isolation, Structure, Synthesis and Antimitotic Properties of Combretastatins B–3 and B–4 from *Combretum Caffrum*" Journal of Natural Products 51:3 (May 1988) 517–527.
Green, Richard H. "Syntheses of Differanisole A" Tetrahedron Letters 38:26 (1997) 4697–4700.
Reddy et al. "From Styrenes to Enanitopure α–Arylglycines in Two Steps" J. Am. Chem. Soc. 120 (Aug. 1997) pp. 1207–1217.

* cited by examiner

*Primary Examiner*—Paul J. Killos
*Assistant Examiner*—Hector M. Reyes
(74) *Attorney, Agent, or Firm*—Mayer Brown Rowe & Maw LLP (57) ABSTRACT

Compounds are provided that lower blood glucose concentrations, lower serum triglyceride concentrations, lower systolic blood pressure, and increase glucose uptake by adipose tissue, but do not affect the expression of PPAR-γ by adipose tissue.

6 Claims, 4 Drawing Sheets

COMPOUNDS TO TREAT DIABETES AND ASSOCIATED CONDITIONS

CROSS REFERENCE TO RELATED APPLICATION

This application is a divisional application based on U.S. Ser. No. 09/436,047, filed Nov. 8, 1999, now U.S. Pat. No. 6,525,093 which issued on Feb. 25, 2003, the entirety of which is incorporated herein by reference.

BACKGROUND OF THE INVENTION

The present application is directed to novel antidiabetic compounds.

The causes of Type I and Type II diabetes are still unknown, although both genetic and environmental factors seem to be involved. Type I diabetes (or insulin-dependent diabetes) is an autonomic immune disease in which the responsible autoantigen is still unknown. Patients with Type I diabetes need to take insulin intravenously to survive. Type II diabetes (formerly referred to as non-insulin dependent diabetes) is a metabolic disorder resulting from the body's inability either to make a sufficient amount of insulin or to properly use the insulin that is produced. Insulin secretion and insulin resistance are considered the major metabolic defects, but the precise genetic factors involved remain unknown.

Patients with diabetes usually have one or more of the following defects:
- Under-production of insulin by the pancreas
- Over-secretion of glucose by the liver
- Defects in glucose transporters
- Desensitization of insulin receptors
- Defects in metabolic breakdown of polysaccharides

In addition to the IV administration of insulin, currently available medications used for diabetes include 4 classes of oral hypoglycemic agents listed in the following table.

| Class | Marketed Drugs | Mechanism of Action | Limitations |
|---|---|---|---|
| Sulfonyl-ureas | First generation: 2 Second generation: 3 | Signals beta cells to release more insulin | Development of resistance Hypoglycemia |
| Bi-guanides | Metformin | Reduces hepatic glucose production Improves Improves sensitivity to insulin | Adverse hepatic effects Lactic acidosis Unwanted Unwanted gastrointestinal effects |
| Glu-cosidase inhibitors | Acarbose | Reduces glucose absorption from gut | Works only after meals GI side effects |
| Thia-zoli-dinediones | Troglitazone Rosi-glitazone Pia-glitazone | Reduce insulin resistance | Not effective in 25% of patients Require frequent liver function tests Have very long onset of action Cause weight gain |

As is apparent from the above table, there are disadvantages to each of the currently available agents for use in the treatment of diabetes. Accordingly, there is a continuing interest in the identification and development of new agents, particularly orally administered, water-soluble agents that can be used for the treatment of diabetes.

SUMMARY OF THE INVENTION

Compounds having the general formula (I)–(III) have glucose-lowering activity.

(I)

Stereocenters (designated by *) could be R— or S—.

Each bond represented by dotted lines could be a double or a single bond, and the geometry across the bond could be E or Z.

R and R' are independently H or $C_1$–$C_{20}$ linear or branched alkyl or alkenyl groups that may be substituted, or functional groups like $COOR_3$, where $R_3$=H, a cation, $C_1$–$C_{20}$ linear or branched alkyl or $C_5$–$C_{10}$ aryl; $CONR_1R_2$, where $R_1$ and $R_2$ may be independently or together H, linear or branched $C_1$–$C_{20}$ alkyl or $C_5$–$C_{20}$ aryl, $NH_2$, OH, $C_1$–$C_{20}$ linear or branched alkoxy, halo, cyano, or R+R'=O.

A, A', A", and C are independently H, $C_1$–$C_{20}$ acylamino, $C_1$–$C_{20}$ acyloxy, linear or branched $C_1$–$C_{20}$ alkanoyl, $C_3$–$C_{20}$ alkoxycarbonyl, $C_1$–$C_{20}$ linear or branched alkoxy; $C_1$–$C_{20}$ linear or branched alkylamino, $C_1$–$C_{20}$ alkylcarboxylamino, $C_1$–$C_{20}$ carbalkoxy; carboxyl, cyano, halo, hydroxy; and n, m, p and v are independently integers from 0 to 3;

B, B', and B" are independently H, $C_1$–$C_{20}$ acylamino, $C_1$–$C_{20}$ acyloxy; $C_1$–$C_{20}$ linear or branched alkanoyl, $C_1$–$C_{20}$ linear or branched alkenyl, $C_1$–$C_{20}$ alkoxycarbonyl, $C_1$–$C_{20}$ linear or branched alkoxy; $C_1$–$C_{20}$ linear or branched alkyl amino, $C_1$–$C_{20}$ alkyl carboxyl amino, $C_1$–$C_{20}$ carbalkoxy; aroyl, araalkanoyl, carboxyl, cyano, halo, hydroxy; and q, r and s are independently integers from 0 to 3;

with the proviso that when m, n, p , q, r, s and v are zero, any unsubstituted positions on the aromatic rings are satisfied with hydrogen;

R", R'" and R"" are independently H, $C_1$–$C_{20}$ linear or branched alkyl or alkenyl groups which may contain substituents, COOH, $C_1$–$C_{20}$alkoxycarbonyl, $NH_2$, $CONH_2$, $C_1$–$C_{20}$ acylamino, OH, $C_1$–$C_{20}$ alkoxy, halo, or cyano.

X=NH, O, S, S=O, or SO$_2$.

(II)

Stereocenters (designated by *) could be R— or S—.

Each bond represented by the dotted line could be a double or a single bond, and the geometry across it may be E or Z.

A, A', and C are independently H, C$_1$–C$_{20}$ acylamino, C$_1$–C$_{20}$ acyloxy, C$_1$–C$_{20}$ alkoxycarbonyl, C$_1$–C$_{20}$ alkoxy, C$_1$–C$_{20}$ linear or branched alkyl amino, C$_1$–C$_{20}$ alkylcarboxylamino, C$_1$–C$_{20}$ carbalkoxy; carboxyl, cyano, halo, hydroxy; and t, u, and w are independently integers from 0 to 3;

B and B' are independently H, C$_1$–C$_{20}$ acylamino, C$_1$–C$_{20}$ acyloxy; C$_1$–C$_{20}$ alkanoyl, C$_1$–C$_{20}$ alkenoyl, C$_1$–C$_{20}$ alkenyl, C$_1$–C$_{20}$ alkoxycarbonyl, C$_1$–C$_{20}$ linear or branched alkoxy, C$_1$–C$_{20}$ linear or branched alkyl amino, C$_1$–C$_{20}$ alkylcarboxylamino, C$_1$–C$_{20}$ carbalkoxy, C$_6$–C$_{20}$ aroyl, C$_6$–C$_{20}$ araalkanoyl, carboxyl, cyan, halo, hydroxy; and x and y are independently integers from 0 to 3;

with the proviso that when t, u, w, x and y are zero, any unsubstituted positions on the aromatic rings are satisfied with hydrogen;

R', R", and R'" are independently H or C$_1$–C$_{20}$ linear or branched alkyl or alkenyl groups which may contain substituents, COOH, C$_1$–C$_{20}$ alkoxycarbonyl, NH$_2$, CONH$_2$, C$_1$–C$_{20}$ acylamino, C$_1$–C$_{20}$ alkoxycarbonyl, OH, C$_1$–C$_{20}$ alkoxy, halo or cyano.

X=NH, O, S, S =O, or SO$_2$.

(III)

Stereocenters (designated by *) could be R— or S—.

The bond represented by the dotted line could be a double or a single bond, and the geometry across it may be E or Z.

A and C are independently H, C$_1$–C$_{20}$ acylamino, C$_1$–C$_{20}$ acyloxy, C$_1$–C$_{20}$ linear or branched alkanoyl, C$_1$–C$_{20}$ alkoxycarbonyl, C$_1$–C$_{20}$ linear or branched alkoxy, C$_1$–C$_{20}$ linear or branched alkyl amino, C$_1$–C$_{20}$ alkylcarboxylamino, C$_1$–C$_{20}$ carbalkoxy; carboxyl, cyano, halo, hydroxy; thiol, SOR or SOR$_2$; and f and g are independently integers from 0 to 3;

B is independently H, C$_1$–C$_{20}$ acylamino, C$_1$–C$_{20}$ acyloxy; C$_1$–C$_{20}$ linear or branched alkanoyl, C$_1$–C$_{20}$ linear or branched alkenoyl, C$_1$–C$_{20}$ linear or branched alkenyl, C$_1$–C$_{20}$ alkoxycarbonyl, C$_1$–C$_{20}$ linear or branched alkoxy, C$_1$–C$_{20}$ linear or branched alkyl amino, C$_1$–C$_{20}$ alkylcarboxylamino, C$_1$–C$_{20}$ carbalkoxy, C$_5$–C$_{20}$ aroyl, C$_6$–C$_{20}$ araalkanoyl, carboxyl, cyan, halo, hydroxy; and e is an integer from 1 to 3:

with the proviso that when f and g are zero, any unsubstituted positions on the aromatic rings are satisfied with hydrogen;

R', R", and R'" are independently H or C$_1$–C$_{20}$ linear and branched alkyl or alkenyl groups which may contain substituents, COOH, C$_1$–C$_{20}$ alkoxycarbonyl, NH$_2$, CONH$_2$, C$_1$–C$_{20}$ acylamino, C$_1$–C$_{20}$ alkoxycarbonyl, OH, C$_1$–C$_{20}$ alkoxy, halo, cyano.

DESCRIPTION OF THE PREFERRED EMBODIMENTS

In the compounds of the formulas I, II and III, the alkyl groups may be linear or branched including but not limited methyl, ethyl, propyl, isopropyl, sec-butyl, n-butyl, pentyl, isopentyl, and the like. Alkenyl groups of 1 to 20 carbon atoms includes but is not limited to, ethylene, propylene, butylene, isobutylene, and the like. Aryl groups include phenyl, and other multi-ring aromatic structures. Alkoxy includes methoxy, ethoxy propoxy, isopropoxy, n-butoxy, isobutoxy and the like. Halo includes bromo chloro, fluoro, iodo.

Acylamino includes the group wherein R could be hydrogen, alkyl or aryl.

Acyloxy includes the group wherein R is hydrogen, alkyl or aryl.

Alkanoyl includes the group wherein R can be hydrogen, alkyl or aryl.

Alkoxy carbonyl includes the group wherein R can be alkyl.

Alkylamino includes the group wherein the amino group may be mono or di-substituted with alkyl groups.

Alkylcarboxylamino includes the group wherein R can be an alkyl group.

Carboalkoxy includes the group wherein R is an alkyl group.

Aroyl includes the group wherein R is aryl.

Araalkanoyl includes the group wherein R is aryl and $R^1$ is alkylenyl.

Preferred compounds of formula are those wherein C and A are hydrogen, and q=2 when B is methyl. Other preferred compounds are those in which A' is hydrogen and r=0, and in which A" is hydrogen and s=0. Another preferred class of compounds comprises those in which R is hydrogen and R' is —$COOR_3$. A preferred class of substituent comprises those in which R"" is hydrogen, R'" and R"" are independently —$COOR_3$ and X is oxygen.

The method used for the synthesis of the representative member of the Type (I) compounds is shown in Scheme I.

Scheme I

A specific method for the synthesis of a representative number of compounds of the formula I is shown below in Scheme IA. Compounds of the formula II where made starting from the second step showing in Scheme I with the appropriate starting materials. The compounds of formula III may be made by utilizing the chemistry of the last step of Scheme I using the appropriate starting materials.

Scheme IA

The compounds of the present invention are useful in the treatment of diseases or disorders characterized by the presence of the elevated blood glucose levels, that is hyperglycemic disorders, such as diabetes melitis, including both type I and II diabetes as well as other hyperglycemic related disorders such as obesity, increased cholesterol kidney related disorders, and the like. The compounds are preferably administered at least to reduce the blood glucose level in the host suffering from the hyperglycemic disorder. The sufficient amount of the compound is administered to the subject to reduced the blood glucose level to an acceptable range which is typically about plus or minus 10%, usually plus or minus 8%, and more usually plus or minus 5% of the normal average blood glucose level for the subject. A variety of hosts may be treated with the compounds to reduce blood glucose levels, such as humans and including mammalians hosts such as livestock, valuable or rare animals and pets, such as dogs and cats. The compounds may be administered by any convenient administration technique including, but not limited to, intravenous, intradermal, intramuscular, subcutaneous, or oral. The dosage delivered to the host will necessarily depend upon the route by which the compound is administered but will generally range from about 50–500 mg/70 kg human body weight, and usually from about 100–200 mg/70 kg human body weight.

The compounds will be combined in a physiologically acceptable vehicle to produce a pharmaceutical composition. The nature of the physiologically acceptable vehicle will necessarily depend on the method for which the pharmaceutically composition is administered. Exemplary vehicles include water, that is, sterile water for injection, saline, such as phosphate buffered saline, lyophilized powder in the form of tablets or capsules where such forms may include various fillers, binders and the like. The amount of the active compound in the pharmaceutical composition will be selected in view of the method by which the pharmaceutical composition is to be administered, and may be determined empirically by those of ordinary skill in the art.

FIGS. 1 through 5 present the results of preclinical tests performed using a compound according to the present invention, 4-(1-carboxy-2-(3,5-dimethoxyphenyl)) ethylenyl-4'-(2,2-dicarbomethoxy) ethyl diphenyl ether.

Figure 1:
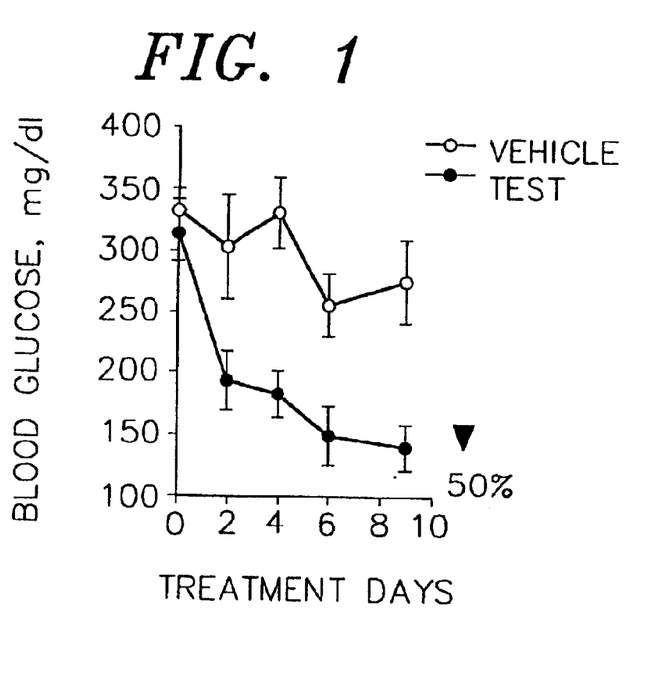
FIG. 1 shows the blood glucose concentrations found in ob/ob mice given the representative compound at a dose of 50 mg/kg for 7 days.

When 6-week-old male ob/ob mice were given a 50 mg/kg dose of this compound or the vehicle daily for 7 days, the blood glucose concentrations of the mice given the compound were reduced 50% from those of the mice given the vehicle only, and the reductions of blood glucose concentrations were observed as early as Day 2 (see FIG. 1).

Figure 2:
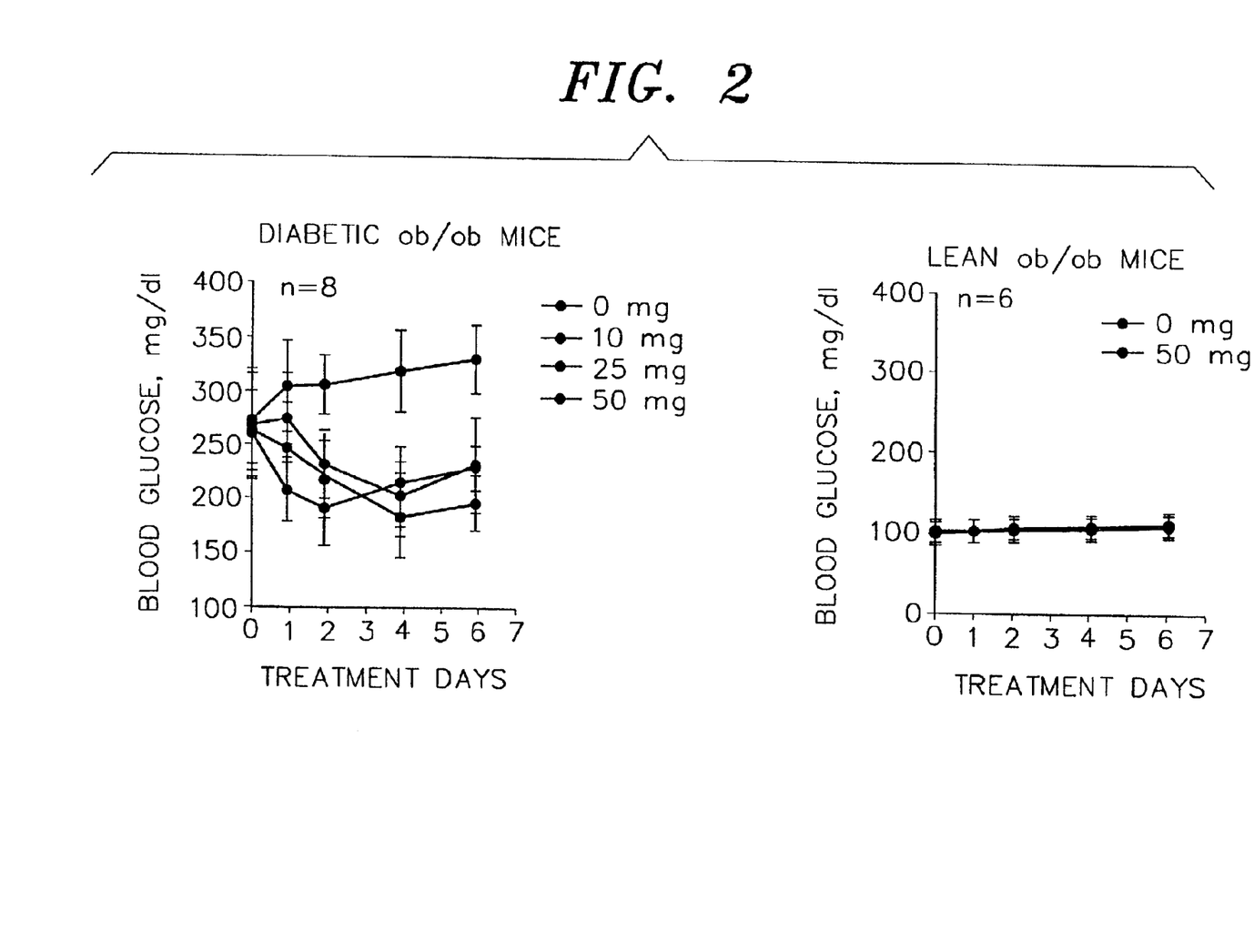
FIG. 2 shows the blood glucose concentrations found in diabetic ob/ob mice given the representative compound at doses of 0 (vehicle), 10, 25, or 50 mg/kg for 7 days (left); and those found in lean ob/ob mice given the representative compound at a dose of 50 mg/kg for the same period (right).
Figure 3:
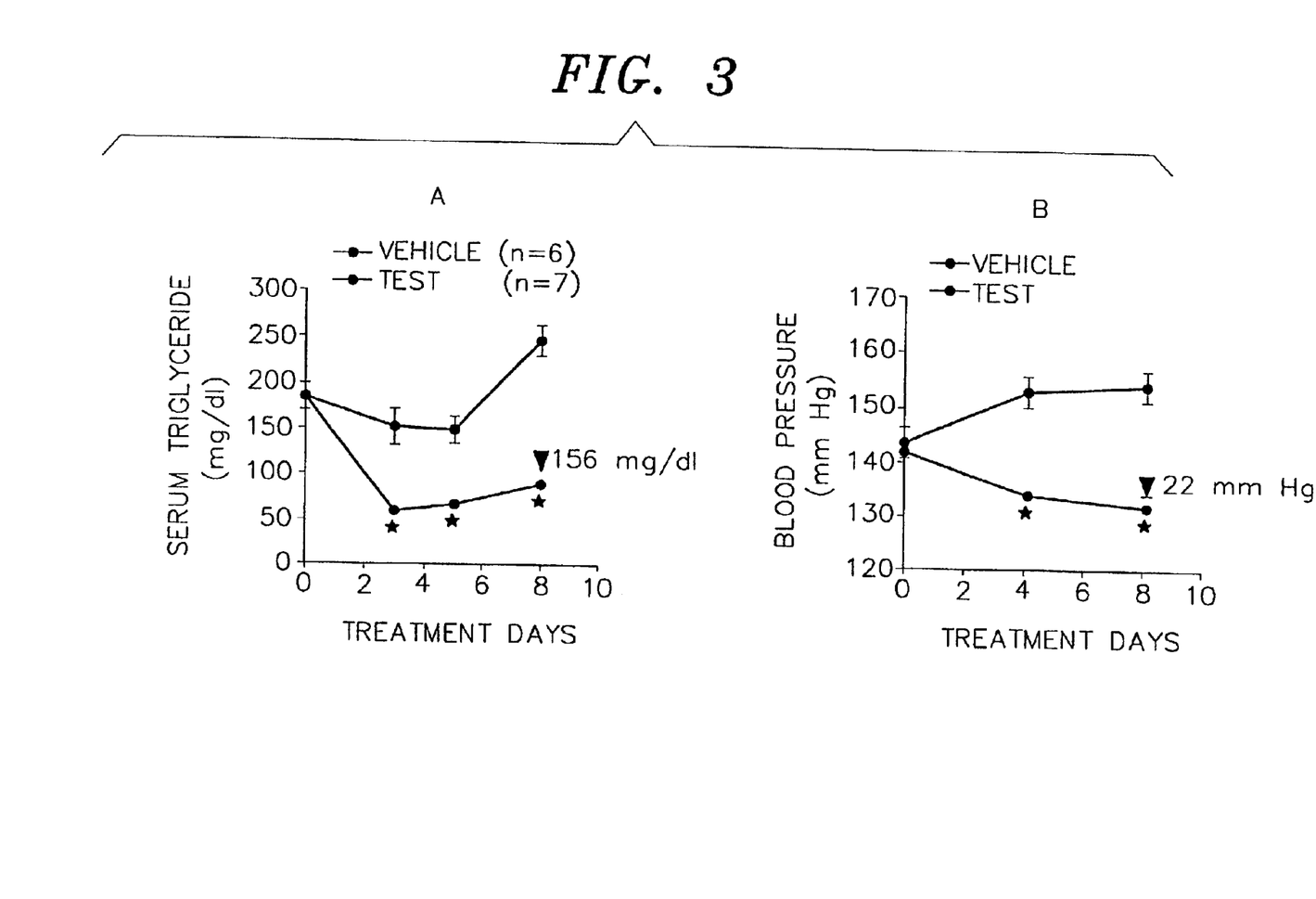
FIG. 3 shows the serum triglyceride concentrations and systolic blood pressure of fructose-fed, insulin-resistant rats that received the representative compound or the vehicle for 7 days.

In another experiment, 6-week-old male diabetic ob/ob mice received the indicated oral doses of the test compound daily. FIG. 2 shows that the 10 mg/kg dose of the compound lowered blood glucose concentrations as effectively as the 50 mg/kg dose. The blood glucose concentrations in lean control animals given the highest dose of the test compound (50 mg/kg) did not differ from those in animals given vehicle only.

The ability of this test compound to lower serum triglyceride concentrations and blood pressure was studied in fructose-fed, insulin-resistant rats. For this experiment, male Sprague-Dawley rats initially weighing 150–175 g were placed on a 60% fructose-enriched diet for 10 days. On Day 11, rats with hypertriglyceridemia were randomly assigned to receive oral doses of vehicle or the compound (50 mg/kg) daily for 7 consecutive days. Serum triglyceride concentrations were measured 24 hours after each administration of test agent, and blood pressure was measured 18 hours after test agent administration. FIG. 3A shows that the test compound effectively lowered serum triglyceride concentrations in these rats, and FIG. 3B shows that the rats treated with the test compound had significantly lower blood pressure than did those treated with vehicle.

Figure 4:
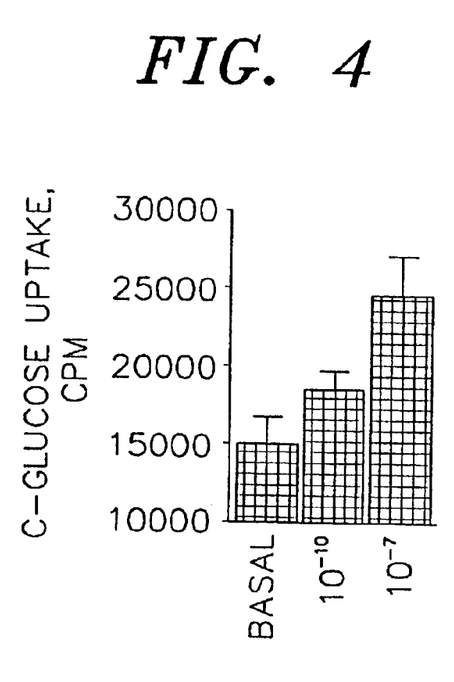
FIG. 4 shows the glucose uptake of 3T3-L1 cells exposed to two different concentrations of the representative compound (0.1 nM and 0.1 µM).
Figure 5:
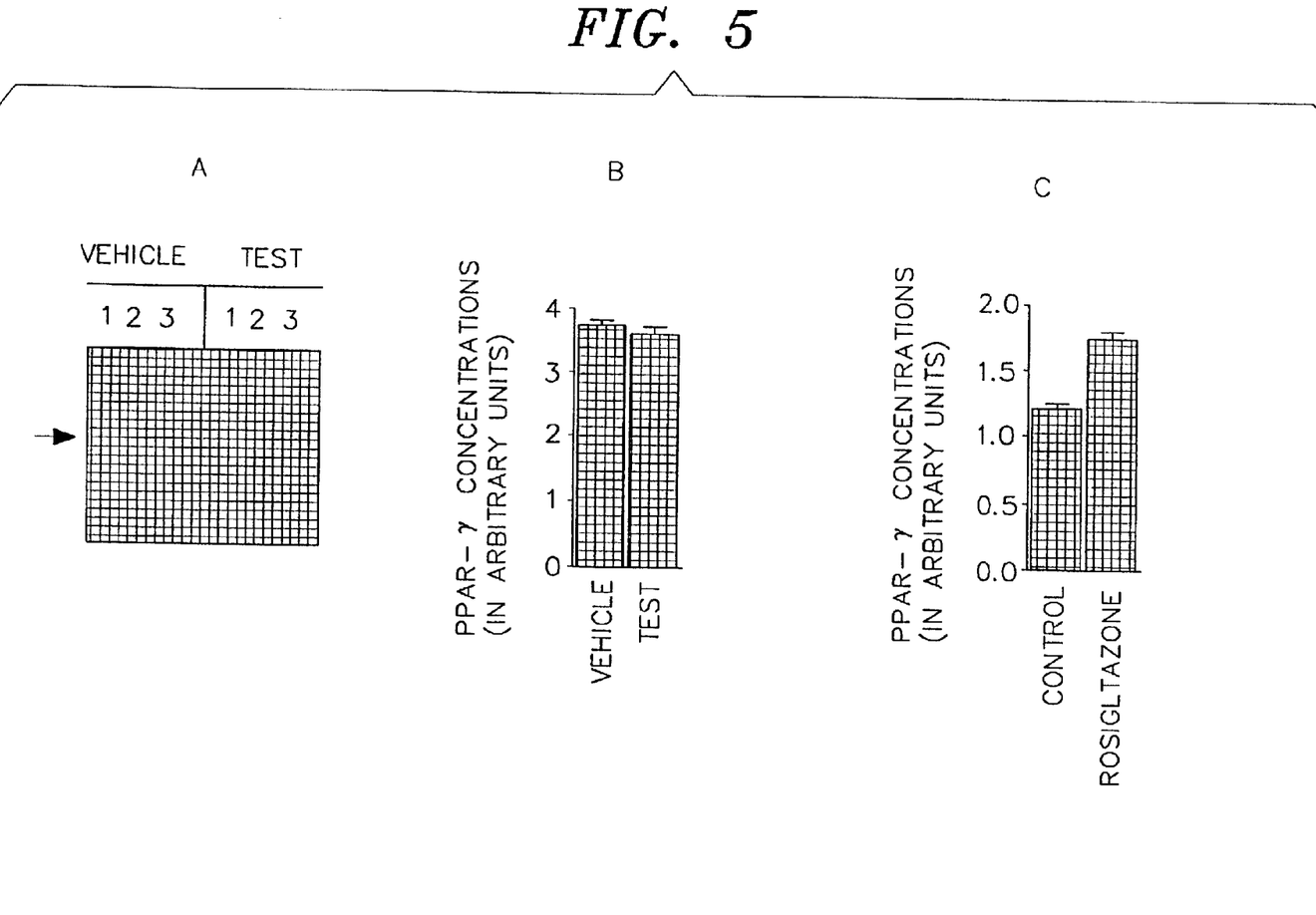
FIG. 5 shows the levels of PPAR-γ expression found in adipose tissue of ob/ob mice treated with the vehicle or the representative compound (50 mg/kg) for 10 days.

Basal glucose uptake of 3T3-L1 cells was measured in the presence of two different concentrations of the test compound (0.1 nM and 0.1 $\mu$M). Cells were incubated at 37° C. for 48 hours with vehicle or the test compound, and then further incubated with $^{14}$C-deoxyglucose for an additional 30 min at 22° C. The cells were washed and lysed, and the total radioactivity in the cells was measured. FIG. 4 shows that the glucose uptake increased over the basal level in cells treated with the test compound. This result suggests that this test compound stimulates glucose uptake in differentiated adipocytes.

In an experiment studying the expression of PPAR-$\gamma$ in the adipose tissue of mice, epididymal fat was collected from six different ob/ob mice either treated with vehicle or the test compound (50 mg/kg) for 10 days, homogenized in lyses buffer, and centrifuged. A total of 30 mg of protein was loaded on to SDS polyacrylamide gel, immunoblotted, and probed with anti PPAR-γ antibody raised against a 15-residue synthetic peptide containing conserved sequences of PPAR-γ (see FIG. 5A). The bands were quantified and represented in bar graphs (see FIG. 5B). The expression levels of PPAR-γ in the tissues from vehicle-treated and the compound-treated animals did not differ from each other.

The tests described above and illustrated in the figures show that the compounds according to the present invention lower blood glucose concentrations, lower serum triglyceride concentrations, lower systolic blood pressure, and increase glucose uptake by adipose tissue, but do not affect the expression of PPAR-γ by adipose tissue.

What is claimed is:

1. A method for lowering blood glucose in a subject comprising administering to said subject an effective blood glucose lowering amount of a compound represented by formula II:

(II)

wherein stereocenters *, if present, are R or S;
dotted lines indicate that a double bond is absent;
A, A', and C are H;
B and B' are H;
R', R", and R'" are H or $C_1$–$C_{20}$ alkoxycarbonyl;
t, x, y and u represent the integer 2;
w represents the integer 1; and
X═O.

2. A method for lowering serum triglyceride in a subject comprising administering to said subject an effective serum triglyceride lowering amount of a compound represented by formula II:

(II)

wherein stereocenters *, if present, are R or S;
dotted lines indicate that a double bond is absent;
A, A', and C are H;
B and B' are H;
R', R", and R'" are independently H or $C_1$–$C_{20}$ alkoxycarbonyl;
t, x, y and u represent the integer 2;
w represents the integer 1; and
X═O.

3. A method for lowering blood pressure in a subject comprising administering to said subject an effective blood pressure lowering amount of a compound represented by formula II:

(II)

wherein stereocenters *, if present, are R or S;
dotted lines indicates that a double bond is absent;
A, A', and C are H;
B and B' are H;
R', R", and R'" are independently H or $C_1$–$C_{20}$ alkoxycarbonyl;
t, x, y and u represent the integer 2;
w represents the integer 1; and
X═O.

4. The method of claim 1 wherein said alkoxycarbonyl is methoxycarbonyl.

5. The method of claim 2 wherein said alkoxycarbonyl is methoxycarbonyl.

6. The method of claim 3 wherein said alkoxycarbonyl is methoxycarbonyl.

* * * * *

UNITED STATES PATENT AND TRADEMARK OFFICE
CERTIFICATE OF CORRECTION

PATENT NO. : 6,855,732 B2
APPLICATION NO. : 10/075442
DATED : February 15, 2005
INVENTOR(S) : Partha Neogi et al.

It is certified that error appears in the above-identified patent and that said Letters Patent is hereby corrected as shown below:

On the title page, item: (75), Inventors, "Debendranath Dev" should be changed to --Debendranath Dey--.

Column 2, line 34, "$R_3$══H," should be changed to --$R_3 = H$,--; line 38, "R + R' ══ O" should be changed to -- R+R' = O--.

Column 3, lines 1 and 42, each occurrence of "X══NH," should be changed to -- X = NH,--.

Column 5, line 47, "q══2," should be changed to --q = 2--; line 48, "r══ O," should be changed to --r = 0--; line 49, "s══O," should be changed to --s = 0--.

Column 7, line 65, "mammalians" should read --mammalian--.

Column 9, line 50 (claim 1), "X══O" should be changed to --X = O--.

Column 10, line 22 (claim 2) and line 47 (claim 3), each occurrence of "X══O" should be changed to --X = O--.

Column 5, line 46, "compounds of formula are" should be changed to "compounds of formula I are"; line 52, "hydrogen, R'''' and R'''' are" should be changed to --hydrogen, R''' and R'' are--.

Column 6, line 52 (Scheme I, final formula), the uppermost R''' should be R''. Although this was drawn correctly in the Substitute Specification filed September 24, 2004, in the mark-up copy it referred to the earlier Preliminary Amendment filed February 15, 2002. There seems to have been a printing problem with some of the pages I received in that Preliminary Amendment, which caused some of the characters to be duplicated. Anyway, in my copy this group does appear to be R''' instead of R'', although it is difficult to read.

UNITED STATES PATENT AND TRADEMARK OFFICE
CERTIFICATE OF CORRECTION

PATENT NO. : 6,855,732 B2
APPLICATION NO. : 10/075442
DATED : February 15, 2005
INVENTOR(S) : Partha Neogi et al.

It is certified that error appears in the above-identified patent and that said Letters Patent is hereby corrected as shown below:

Column 9, line 2, "30 mg" should be changed to --30 μg--.

Signed and Sealed this

Fifteenth Day of August, 2006

JON W. DUDAS
*Director of the United States Patent and Trademark Office*